US008491554B2

(12) United States Patent
Carlucci et al.

(10) Patent No.: US 8,491,554 B2
(45) Date of Patent: Jul. 23, 2013

(54) TRANSPARENT ABSORBING ARTICLE

(75) Inventors: Giovanni Carlucci, Chieti (IT);
Roberto D'Addario, Pianella (IT);
Ivano Gagliardi, Pescara (IT)

(73) Assignee: The Procter and Gamble Company, Cincinnati, OH (US)

( * ) Notice: Subject to any disclaimer, the term of this patent is extended or adjusted under 35 U.S.C. 154(b) by 2712 days.

(21) Appl. No.: 10/239,599

(22) PCT Filed: Mar. 21, 2001

(86) PCT No.: PCT/US01/09329
§ 371 (c)(1),
(2), (4) Date: Sep. 23, 2002

(87) PCT Pub. No.: WO01/72252
PCT Pub. Date: Oct. 4, 2001

(65) Prior Publication Data
US 2003/0065299 A1  Apr. 3, 2003

(30) Foreign Application Priority Data

Mar. 25, 2000  (EP) ..................................... 00106495
Jul. 19, 2000  (EP) ..................................... 00115522

(51) Int. Cl.
*A61F 13/15*  (2006.01)
*A61F 13/20*  (2006.01)
(52) U.S. Cl.
USPC .................. 604/385.04; 604/385.01; 604/367

(58) Field of Classification Search
USPC ................ 604/359–362, 367, 385.01, 385.04
See application file for complete search history.

(56) References Cited

U.S. PATENT DOCUMENTS

| 2,881,761 | A |   | 4/1959  | Kenner |
|-----------|---|---|---------|--------|
| 4,463,045 | A | * | 7/1984  | Ahr et al. ...................... 428/131 |
| 5,364,381 | A | * | 11/1994 | Soga et al. ..................... 604/366 |
| 5,647,863 | A | * | 7/1997  | Hammons et al. ............. 604/378 |
| 5,665,452 | A |   | 9/1997  | Langdon et al. |
| 5,728,125 | A |   | 3/1998  | Salinas |
| 5,897,541 | A |   | 4/1999  | Uitenbroek et al. |
| 5,947,943 | A |   | 9/1999  | Lee |
| 6,511,464 | B1 |  | 1/2003  | Suekane |
| 6,659,991 | B2 |  | 12/2003 | Suekane |
| 7,034,199 | B2 |  | 4/2006  | Suekane et al. |

FOREIGN PATENT DOCUMENTS

| DE | 42 26 739 A 1 |   | 2/1997 |
|----|---------------|---|--------|
| DE | 200 01 141 U 1 |  | 4/2000 |
| EP | 0 925 769 A2 |   | 6/1999 |
| EP | 1 078 619 A2 |   | 2/2001 |
| GB | 2 303 291 A |    | 2/1997 |
| JP | 08-71101 A |     | 3/1996 |
| JP | 10-085757 A |    | 4/1998 |
| JP | 10-298321 |      | 11/1998 |
| WO | WO 94/24557 A1 | | 10/1994 |
| WO | 9610380 |  * | 4/1996 |

* cited by examiner

*Primary Examiner* — Michele M Kidwell
(74) *Attorney, Agent, or Firm* — Andrew J. Hagerty; Megan C. Hymore; Jason J. Camp

(57) ABSTRACT

The present invention relates to absorbent articles, such as pantiliners or sanitary napkins, which have at least one region of the article which is transparent to visible light. In one embodiment to whole article is transparent.

5 Claims, No Drawings

TRANSPARENT ABSORBING ARTICLE

FIELD OF THE INVENTION

The present invention relates to transparent absorbent articles such as pantiliner or sanitary napkins which have at least regions of the liner or napkin made from materials which are transparent to visible light.

Such transparent or partially transparent articles have the benefit of not becoming easily apparent by visual inspection even if they are worn with colored (i.e. not white) undergarments.

BACKGROUND OF THE INVENTION

It has historically been common that absorbent articles, in general including diapers, adult incontinence products, underarm sweat products, collar inserts, sanitary napkins and pantiliners are provided in a color communicating a hygienic condition. This conventionally resulted in white or predominantly white articles. This did fit well with the historically predominant undergarment color in which these articles are worn namely white undergarments. As a result white pantiliners or white sanitary napkin are not easily recognizable when used in such white undergarments.

Very recently fashion has led women more frequently to use other colors than white undergarments. This has been dictated not only by fashion itself but also as a result of the development of clothing which has a certain translucency and allows the color of the undergarment to be recognized. Consequently, it has become more desirable to use undergarments of a matching color or of a skin color. Furthermore very recently so-called G-String undergarments or "Tanga-Slips" have become widely used in particular by a younger generation women, which are all in the fertile, i.e. menstruating, age group. These so-called string tangas are particularly used to prevent easy recognition of the contour of the undergarment through tight fitting clothes. For these undergarments it is also highly desirable to have sanitary napkins or pantiliners available which match the color of these garments in order to prevent a color-based recognition of the presence of such articles (under the assumption that modern clothing can be translucent).

It is therefore quite apparent that a colored sanitary napkin or pantiliner matching the color of the undergarment would be desirable. For sanitary napkins or pantiliners having so-called wings which are folded around the outside of the undergarment this is even more important since the wing part of the sanitary napkin or pantiliner is on purpose folded onto the outside of the undergarment and therefore easily visible, depending on the clothing worn over the undergarment.

This, however, conflicts drastically with the possibilities of manufacturers of such articles. First of all the number of colors is inevitably very large, since in particular black, dark brown, light brown, red, green, blue and—more fashion oriented—purple undergarments are broadly available. In order to provide such a variety of colors, multiplied by the number of different product sizes to cater for the different needs of the user would mean for a manufacturer to have an extremely large number of articles which have to made and stocked. At the same time the shops in which such products would be sold would have to provide enormous space in order to stock and offer each variety for the potential customer.

Therefore the problem exists as to how to provide a sanitary napkin or pantiliner such that its color does not create a highlight, relative to the color of the undergarment in which it is worn. In other words: an at least partially invisible sanitary napkin or pantiliner would be desirable.

EP 322 309 describes a disposable clothing shield to protect clothing from stains which is visibly masked through the clothing. This is achieved by providing a thin shield which has an outer surface which randomly scatters light reflected from it so that the shape is not reflected or radiated therefrom. This is achieved by a complicated method of providing randomly dispersed white spunbonded fibres onto a beige colored thermoplastic film layer.

It is therefore an objective of the present invention to provide absorbing articles, particularly sanitary napkins or pantiliners which are made such that when worn they are not easily recognizable due to the color difference to the undergarment or more generally under the garment in which they are worn, which are simple and cheap to mass manufacture.

BRIEF DESCRIPTION OF THE INVENTION

The present invention relates to absorbing articles such a sanitary napkins or pantiliners which are provided with at least one region which is transparent. Transparency is provided to these articles by the use of transparent materials.

A second or alternative aspect of the present invention are absorbing articles such as sanitary napkins or pantiliners provided with wings, which are transparent. According to the present invention such wings, together with the remainder of the article or separately, are provided by transparent material.

DETAILED DESCRIPTION OF THE INVENTION

Definitions

"Absorbing articles" as referred to herein are primarily sanitary napkins, pantiliners, or incontinence pads which are worn in the crotch region of a undergarment. However, articles such as sweat-absorbent underarm pads, nursing pads or collar inserts can also benefit from the present invention. It is even conceivable that baby diapers, adult incontinence diapers, and human waste management devices benefit from the present invention even though they are conventionally not worn in conjunction with an undergarment. However, if they are worn in conjunction with an undergarment or covering garment transparency may prevent the immediate visual recognition of their presence (provided their bulkiness does not create immediate recognition).

"Transparent" as used herein refers to the ability of a material or combination of materials to transmit visible light through the body of the material. It is recognized that any material will remove a certain fraction of light and therefore complete transparency cannot exist. Therefore the requirement for transparency according to the present invention is that a color be visually recognizable when viewed by the human eye through the transparent region of the article. There are many various possibilities to measure transparency, one of which is identified below.

According to the present invention said region of transparency should have a transparency value of at least 20%, preferably at least 30%, most preferably at least 40% ($\Delta E$ verses reference).

The absorbing article according to the present invention typically comprises a liquid pervious surface, a liquid impervious surface and an absorbent structure comprised therebetween. Usually, such as in the absorbent articles described herein as examples of the present invention, the liquid pervious surface is provided by a topsheet, the liquid impervious surface is provided by a backsheet and the absorbent structure is provided by an absorbent core. Preferably the absorbent article according to the present invention is conventionally constructed of three main elements: the topsheet, facing the user of the article during use and being liquid pervious in order to allow liquids to pass into the article; the backsheet, providing liquid containment such that absorbed liquid does not leak through the article, this backsheet conventionally provides the garment facing surface of the article; and the absorbent core sandwiched between the topsheet and the backsheet and providing the absorbent capacity of the article to acquire and retain liquid which has entered the article through the topsheet.

Many absorbing articles and constructions, including particular materials, are known in the art and have been described in ample detail over time. All of such materials are useful in the context of the present invention, provided that they allow a minimum degree of transparency to be achieved. Typically this will require only moderate modification of the material composition while maintaining the majority of the conventional material characteristics. In the following examples of materials which are particularly beneficial for the use in transparent absorbing articles according to the present invention are mentioned. Those skilled in the art will readily be able to identify alternative materials which can also be used and which for other reasons than their transparency maybe particularly desirable in the context of transparent absorbing articles according to the present invention.

Topsheet

In general the topsheet is compliant, flexible, soft feeling and non-irritating to the wearer's skin. The topsheet can be made from a nonwoven or woven material or a film which has been rendered liquid pervious by aperturing. Such films and nonwovens or wovens can be made for example from polymers such as polyethylene or polypropylene compositions. Conventionally such polymers have been provided with a coloring material such as titanium dioxide to provide a white opacity. Simply omitting the coloring material from the polymer provides a transparent film or nonwoven which has a high degree of light transmission. The absence of the color filler, such as titanium dioxide, however does not cause any substantial material changes. In fact, it has been mentioned in the art that the desire for a particular white material may cause a polymeric material to have undesirable physical characteristics such as brittleness which have led to a body of art according to which multi-layered films are created in which only some of the layers are provided with a color filler while other layers provide structural stability and integrity but do not comprise the color material. Hence the absence of a color filler in the polymeric material from which the topsheet can be made also provides the additional benefit of better material characteristics (besides less costs and a reduced environment burden). Alternatively, the topsheet may be provided with non white pigmented fillers which impart a tint to the topsheet in a desirable color such as black, red, yellow, blue and green whilst still ensuring the desired transparency. According to the present invention, the region of the topsheet which is transparent preferably contains not more than 1% by weight of said topsheet (including multilayers) of white fillers, preferably not more than 0.5% by weight of white fillers and is most preferably free of white fillers. In embodiments containing non white pigmented fillers, the topsheet typically comprises from 0.1% to 3%, preferably from 0.3% to 0.6% of said filler. An example of non white pigmented fillers is green 7-(74260) CAS 1328753-6.

The topsheet can be completely transparent or can be provided only with regions of transparency. Preferably the topsheet is at least transparent in the region where it extends beyond the absorbent core such that the region of the absorbing article extending beyond the periphery of the absorbent core can be provided with transparency.

Backsheet

In general the backsheet is compliant, flexible and soft feeling. The backsheet prevents the exudes absorbed and contained in the absorbent core from wetting clothes that contact the absorbing article such as an undergarments. Preferably the backsheet is impervious to liquids (e.g., menses, sweat and/or urine). It can be manufactured from a thin plastic film, although other flexible liquid impervious materials can also be used. As used herein, the term "flexible" refers to materials that are compliant and will readily conform to the general shape and contours of the human body. The backsheet preferably also can have elastic characteristics allowing it to stretch in one or two directions.

The backsheet can comprise a woven or nonwoven material, polymeric films such as thermoplastic films of polyethylene or polypropylene, or composite materials such as a film-coated nonwoven material or fiber coated film. Conventionally absorbing articles comprise a backsheet of a polyethylene film having a thickness of from about 0.012 mm to about 0.051 mm.

The backsheet is preferably breathable, i.e. allows the transmission of water vapor, or even more preferable the transmission of air, however without sacrificing its main purpose to provide leakage protection for absorbed liquids. The backsheet can also comprise more than one breathable layer so as to replace a single breathable backsheet layer by at least 2 or 3 layers of a different or the same material. In particular two breathable layers forming together the breathable backsheet are preferred.

According to the present invention such a polyethylene backsheet, or in fact any backsheet made from polymeric material can be provided with transparency by eliminating the white color filler, which conventionally was, for white materials, titanium dioxide. As will be recognized by those skilled in the art the transparency of the backsheet can be provided in the same fashion as in the topsheet and may comprise non white pigmented fillers.

As with the topsheet the entire backsheet can be completely transparent or it may also only be provided with regions of transparency. Preferably, the region of transparency of the backsheet corresponds to the transparency region provided in the topsheet as otherwise the transparency of the overall product would suffer. Therefore the transparency of the backsheet is preferably provided at least in the region in which the backsheet extends beyond the periphery of the absorbent core, which is the region where the backsheet conventionally is joined to the topsheet.

In one embodiment of the present invention the topsheet and the backsheet are completely transparent over their entire surfaces. This not only provides the previously mentioned benefits of a transparent peripheral edge of the product, but also allows the wearer of such a product to be able to observe the core and the absorbent liquid contained therein. As a result the wearer can readily identify if the absorbent capacity of the product has been reached and accordingly decide on when to replace the absorbent article with a new one for self comfort and cleanness.

Absorbent Core

The absorbent core of the transparent absorbing articles according to the present invention may or may not be provided with a region of transparency. In cases where the transparent region of the absorbent article is outside the region co-extensive with the absorbent core, then the absorbent core need not be transparent and can be provided in any conventional fashion known. An example of such cores is provided below. This is particularly preferable for absorbing articles in which only those parts of the absorbent article which are not co-extensive with the absorbent core are desired to be transparent, for example in an embodiment where a sanitary napkin is provided with transparent wings or a transparent peripheral region.

In the alternative if all or part of the region of the article co-extensive with the absorbent core is desired to be transparent then of course the absorbent core itself must support this transparency and materials such as polymeric fibers or superabsorbent materials such as hydrogels which are conventionally and frequently used, need to support this transparency by being provided in a transparent form, i.e. without a white color filler such as titanium dioxide as has been explained above for the topsheet and the backsheet already, for non-white pigmented colors. Where materials for the absorbent core are used which cannot be altered to be transparent it is then necessary to replace these materials by transparent materials having otherwise similar characteristics.

Thus in another preferred embodiment of the present invention the topsheet, backsheet and core are completely transparent over their entire surfaces. The advantage of this embodiment is that it has been surprisingly found that not only is the product not recognizable when worn in combination with colored undergarments and or semi-translucent garments, the contour of the article itself under the garment is no longer discernable. This is especially useful when the articles are worn in combination with tight fitting clothing.

Conventionally the absorbent core can be a single entity or comprise several layers. It can includes the following components: (a) optionally a primary fluid distribution layer; (b) optionally a secondary fluid distribution layer; (c) a fluid storage layer; (d) optionally a fibrous layer underlying the storage layer; and (e) other optional components.

a. Optional Primary Fluid Distribution Layer

One optional component of the absorbent core according to the present invention is the primary fluid distribution layer. This primary distribution layer typically underlies the topsheet (if present) and is in fluid communication therewith. The primary distribution layer acquires body fluid for ultimate distribution to the storage layer. This transfer of fluid through the primary distribution layer occurs mainly in the thickness, but may also provide distribution along the longitudinal and transverse directions of the article.

b. Optional Secondary Fluid Distribution Layer

Also optional according to the present invention is a secondary fluid distribution layer. This secondary distribution layer typically underlies the primary distribution layer and is in fluid communication therewith. The purpose of this secondary distribution layer is to readily acquire bodily fluid from the primary distribution layer and distribute it along the longitudinal and transverse directions of the thong liner before transfer to the underlying storage layer. This helps the fluid capacity of the underlying storage layer to be fully utilized.

c. Fluid Storage Layer

Positioned in fluid communication with, and typically underlying the primary or secondary distribution layers, is a fluid storage layer.

The fluid storage layer may be any absorbent means that is capable of absorbing or retaining liquids (e.g., menses and/or urine). The fluid storage layer may be manufactured in a wide variety of sizes and shapes (e.g., rectangular, oval, hourglass, asymmetric, etc.) and from a wide variety of liquid-absorbent materials commonly used in sanitary napkins and other absorbent articles such as comminuted wood pulp that is generally referred to as airfelt. Examples of other suitable absorbent materials include creped cellulose wadding, modified cross-linked cellulose fibres (such as those described in U.S. Pat. No. 5,217,445 issued to Young, et al. on Jun. 8, 1993), capillary channel fibres (that is, fibres having intra-fibre capillary channels such as those described in U.S. Pat. No. 5,200,248 issued to Thompson, et al. on Apr. 6, 1993), absorbent foams (such as those described in U.S. Pat. No. 5,260,345, issued to DesMarais, et al. on Nov. 9, 1993 and U.S. Pat. No. 5,268,244 issued to DesMarais, et al. on Dec. 7, 1993), thermally bonded airlaid materials (such as those material described in U.S. patent application Ser. No. 08/141,156, entitled "Catamenial Absorbent Structures Having Thermally Bonded Layers For Improved Handling of Menstrual Fluids and Their Use In Catamenial Pads Having Improved Fit and Comfort" filed in the name of Richards, et al. on Oct. 21, 1993), absorbent sponges, synthetic staple fibres, polymeric fibres, hydrogel-forming polymer gelling agents, peat moss, tissue including tissue wraps and tissue laminates, or any equivalent materials or combinations of materials. Suitable fluid storage layers comprising foams are described in European Applications 0 598 833, 0 598 823 and 0 598 834. Suitable fluid storage layers comprising tissue laminates with particles of superabsorbent or gelling agents comprised therebetween are described in International Patent Applications WO 94/01069 and WO 95/17868.

Preferably the fluid storage layer comprises super-absorbent or gelling materials usually referred to as "hydrogels," "superabsorbent", "hydrocolloid" materials. Absorbent gelling materials are those materials that, upon contact with aqueous fluids, especially body fluids, imbibe such fluids and thus form hydrogels. These absorbent gelling materials are typically capable of absorbing large quantities of aqueous body fluids, and are further capable of retaining such absorbed fluids under moderate pressures. In the prior art these absorbent gelling materials are typically in a granular form of discrete, non-fibrous particles. However, according to the present invention these super-absorbent gelling materials can also be provided in non-granular form, preferably in a fibrous form.

In the fluid storage layer these absorbent gelling materials can be dispersed homogeneously or non-homogeneously in a suitable fibrous matrix also referred to as carrier. Suitable carriers include cellulose fibers, in the form of fluff, such as is conventionally utilized in absorbent cores. Modified cellulose fibers such as the stiffened cellulose fibers can also be used. Synthetic fibers can also be used and include those made of cellulose acetate, polyvinyl fluoride, polyvinylidene chloride, acrylics (such as Orion), polyvinyl acetate, non-soluble polyvinyl alcohol, polyethylene, polypropylene, polyamides (such as nylon), polyesters, bicomponent fibers, tricomponent fibers, mixtures thereof and the like. Preferred synthetic and man-made fibers have a denier of from about 3 denier per filament to about 25 denier per filament, more preferably from about 5 denier per filament to about 16 denier per filament. Also preferably, the fiber surfaces are hydrophilic or are treated to be hydrophilic. A non transparent storage layer can also include filler materials, such as Perlite, diatomaceous earth, Vermiculite, etc., that lower rewet problems. Further the storage layer may comprise a binder including but not limited to Latex binders which can be sprayed as an aqueous solution onto the surface of the storage layer prior to curing. If transparency is required, these carrier materials must be selected to provide the desired transparency.

If the absorbent gelling materials are dispersed non-homogeneously in a fibrous matrix, the storage layer can be locally homogeneous, i.e. have a distribution gradient in one or several directions within the dimensions of the storage layer. Non-homogeneous distribution thus includes e.g. laminates of the fibrous carriers enclosing the absorbent gelling materials.

Preferably, the storage layer comprises from 5% to 95% absorbent gelling materials, preferably from 5% to 50%, most preferably from 8% to 35%, absorbent gelling materials. Further the storage layer can comprise from 5% to 95% carrier fibers, preferably from 95% to 50%, most preferably from 92% to 65% carrier fibers.

Suitable absorbent gelling materials for use herein will most often comprise a substantially water-insoluble, slightly crosslinked, partially neutralized, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 (Brandt et al), issued Mar. 31, 1987, and reissued as RE 32,649 on Apr. 19, 1988. Preferred monomers include acrylic acid, methacrylic acid, and 2-acrylamido-2-methyl propane sulfonic acid. Acrylic acid itself is especially preferred for preparation of the superabsorbent material, as it also has a 'natural' transparency which is not optimal but acceptable if the desired transparency is not too high.

Whatever the nature of the basic polymer components of the hydrogel-forming polymeric absorbent gelling materials, such materials will in general be slightly crosslinked. Crosslinking serves to render the hydrogel-forming polymer gelling materials substantially water-insoluble, and crosslinking thus in part determines the gel volume and extractable polymer characteristics of the hydrogels formed from these polymeric gelling materials. Suitable crosslinking agents are well known in the art and include, for example, those described in greater detail in U.S. Pat. No. 4,076,663 (Masuda et al), issued Feb. 28, 1978. Preferred crosslinking agents are the di- or polyesters of unsaturated mono- or polycarboxylic acids with polyols, the bisacrylamides and the di- or triallyl amines. Other preferred crosslinking agents are N,N'-methylenebisacrylamide, trimethylol propane triacrylate and triallyl amine. The crosslinking agent can generally constitute from about 0.001 mole percent to 5 mole percent of the resulting hydrogel-forming polymer material. More preferably, the crosslinking agent will constitute from about 0.01 mole percent to 3 mole percent of the hydrogel-forming polymeric gelling material.

The slightly crosslinked, hydrogel-forming polymeric gelling materials are generally employed in their partially neutralized form. For purposes of the present invention, such materials are considered partially neutralized when at least 25 mole per-cent, and preferably at least 50 mole percent of monomers used to form the polymer are acid group-containing monomers that have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

While these absorbent gelling materials have typically been disclosed in the prior art in granular form, it is possible in the context of the present invention that the absorbent gelling material is in a non-granular form for example as macrostructures such as fibers, sheets or strips. These macrostructures can be prepared by forming the particulate absorbent gelling material into an aggregate, treating the aggregated material with a suitable crosslinking agent, compacting the treated aggregate to densify it and form a coherent mass, and then curing the compacted aggregate to cause the crosslinking agent to react with the particulate absorbent gelling material to form a composite, porous absorbent macrostructure. Such porous, absorbent macrostructures are disclosed, for example, in U.S. Pat. No. 5,102,597 (Roe et al), issued Apr. 7, 1992.

If this absorbent core is desired to be transparent then it can be provided by a layer comprising 100% of an absorbing gelling material. Such gelling material must then be transparent, typical example of transparent absorbent gelling material is a water based hydrogel adhesive which is not saturated with water. Such hydrogel adhesives are known as body adhesives but can be used in a less water saturated form as transparent absorbent cores. An example of such a material is Hydrmelt NP-2257, available from the H. B. Fuller Company, Lüneburg, Germany. Such materials are particularly advantageous in that they also function as a construction adhesive for the article and do not necessitate the addition of construction adhesives between the core, topsheet and backsheet. Alternatively the core can be provided from a transparent fibrous superabsorbent nonwoven. According to a particularly preferred embodiment of the present invention the absorbent core comprises only one layer, preferably one fluid storage layer.

d. Optional Fibrous Layer

An optional component for inclusion in the absorbent cores according to the present invention is a fibrous layer adjacent to, and typically underlying the storage layer. This underlying fibrous layer would typically provide the same function as the secondary fluid distribution layer.

e. Other Optional Components

The absorbent cores according to the present invention can include other optional components normally present in absorbent webs. For example, a reinforcing scrim can be positioned within the respective layers, or between the respective layers, of the absorbent cores. Such reinforcing scrims should be of such configuration as to not form interfacial barriers to fluid transfer, especially if positioned between the respective layers of the absorbent core. Given the structural integrity that usually occurs as a result of thermal bonding, reinforcing scrims are usually not required for the absorbent structures according to the present invention.

Another component which can be included in the absorbent core according to the invention and preferably is provided close to or as part of the primary or secondary fluid distribution layer are odor control agents. Typically active carbon coated with or in addition to other odor control agents, in particular suitable zeolite, silica or clay materials, are optionally incorporated in the absorbent core.

Physical Characteristics of Absorbent Cores

Absorbent cores are usually non extensible and non-elastic, however, they can be rendered extensible and depending on the selected materials can also be made to have elastic characteristics. The term "extensible" as used hereinafter refers to a structure which under external forces such as those occurring during use extends in the direction of the forces or in the direction of a component of the forces in cases where only mono directional extensibility is provided.

The term "elastic" as used hereinafter refers to extensible structures which return at least partially to their initial state after the forces causing the extension cease to be exerted. Absorbent cores can be corrugated or pleated in one or several directions to provide a certain extensibility while selection of elastic fibers for the structure can provide elasticity.

The absorbent cores should preferably be thin. A thickness of less than 5 mm, preferably less than 3 mm, more preferably less than 1.8 mm, and even more preferable between 0.1 and 1.8 mm is desirable such that the resulting articles can also have a low thickness.

In the context of transparency, thinness of the transparent region of the article is also of key importance since the thicker a material is the less transparent it will be.

Absorbing Article Construction

Absorbing articles according to the present invention are constructed like conventional articles with the exception that the conventional means for joining portions of material together must be carefully considered to ensure that the objective of creating a transparent region is not lost. E.g. the adhesive used to join the topsheet to the backsheet in the region outside the absorbent core should either be transparent or it should be eliminated and be replaced by e.g. crimping.

Transparent adhesives are widely available e.g. conventional adhesives can be transparent and many polymer based adhesives are transparent since they have never been used for their opacity and hence their compositions did never include color fillers to start with.

Absorbing Article Design

The transparency as indicated above can be used beneficially in the context of sanitary napkins, panty liners and sweat pads (underarm or collar). A new product design, which is a sub-form of a sanitary napkin or panty liner form, namely thong shaped sanitary napkins or panty liners, so called thong liners, are particularly susceptible to the present invention. The thong liner design is such that it provides the sanitary napkin or panty liner with a shape such that it can be worn in thong slips, G-string undergarments or string panties, hence the thong shape is fundamentally triangular or trapezoidal.

Optional Components of the Absorbing Articles

Optionally, the absorbing articles of the present invention can comprise all those components typical for the intended product use. For example absorbing articles can comprise components such as wings in order to improve their positioning and soiling protection performance especially towards the rear end of the article. Such designs are shown for example in EP 130 848 or EP 134 086, Thong liners with wings are shown in U.S. design No. 394,503, UK designs 2,076,491 and 2,087,071 as well as internationally filed industrial model DM 045544, filed under the Hague Agreement, registered on Oct. 21, 1998.

If present the wings can be the region of the absorbing article which comprises the transparent region. In fact an article design in which the wings are transparent is preferred and in this context, particularly for thong liners, it can be desirable to have transparent wings. The reason is that wings on thong liners extend substantially to the rear end of the article and when folded onto the external side of a thong slip are rather easily visible.

Irrespective whether the wings are specially designed for thong liners or for conventional absorbent articles they can be provided as separate pieces and be attached to the thong liner or they can be integral with the materials of the thong liner, e.g. by being integral extension of the topsheet, the backsheet or a combination thereof. If the wings are attached then they can be attached in a basic outward pointing position or already be predisposed towards their in-use position, i.e. towards the longitudinal centerline. If the wings are integral extensions of the topsheet or the backsheet or both then they are provided with the same transparency as these materials.

In general, all typically used components in absorbent products can also be comprised in the absorbing articles according to the present invention as long as the absorbing article comprises at least one region of transparency.

Most preferred absorbing articles will comprise a fastening adhesive for attachment. The design of the fastening adhesive must be selected such that it does not interfere with the desired transparency but transparent adhesives will ensure that. In the case of sanitary napkins, pantliners or thongliners a so called panty fastening adhesive is preferred to be present on the backsheet for attachment to an undergarment. However, for sweat pads, e.g. underarm sweat pads, either attachment to an adjacent garment or attachment to the skin of the wearer directly can also be considered. Of course, such direct skin attachment, which is conventionally provided by water gel, hydrogel or oil gel based body adhesives, can also be used in sanitary napkins or body liners (in contrast to pantliners).

In a particularly preferred embodiment of the present invention, the absorbing article may further comprise a blood detection composition as described in the Applicant's copending European patent applications 98120476.1, and/or PCT applications PCT/US/00/11208, PCT/US/00/11207, PCT/US/00/11206, PCT/US/00/11204 and PCT/US/00/11205. These compositions are capable of blood detection and provide a visual signal in the form of a color change and typically comprise an oxidisable color indicator and an oxidant such as peroxide or per-acid which is stabilised by a component selected from cyclodextrin or nitrone or combinations thereof. The presence of such a blood detection composition preferably located within the transparent region of the absorbing article is particularly advantageous as it allows the wearer to readily observe the color change of the detection composition.

This effect may be further enhanced by the utilization of transparent regions which are tinted with a particular color such as black, blue, red, green or yellow whilst still maintaining the transparency. The presence of the tinted transparent region will result in a change of color of this region due to the combination with the color indicator. This thereby provides a further signal to the consumer.

Transparent Evaluation

General Definition

Optically transparent: Permitting the passage of light radiation.

Optically transparent medium: A medium which has the property of transmitting rays of lights in such a way that the human eye may see through the medium distinctly.

In general transparency is the ability of a material to transmit light through itself and consequently by the transparency it is possible to see object/colors/printed or written text through such material.

Transparent Product

Accordingly to the above terminology a transparent region of a product is defined by:

1. having the property of transmitting rays of light in such a way that written or printed text/characters and colors located opposite the transparent product can be clearly viewed by the human eye.

and/or 2. having the property of transmitting rays of light in such a way that the human eye may see through the product.

One of the main advantages delivered by a transparent product is that its presence (color) is less recognizable by the human eye, such that, primarily, the color of the undergarment (or other clothing) is recognizable (visual discreteness, no product awareness).

Colors can be measured according an internationally recognised 3D solid diagram of colors where all colors that are perceived by the human eye are converted into a numerical code. This system is based on three dimensions (x,y,z) and specifically L*, a*, b*.

When a color is defined according to this system L* represents lightness (0=black, 100=white), a* and b* independently each represent a two color axis, a* representing the axis red/green (+a=red, −a=green), while b* represents the axis yellow/blue (+b=yellow, −b=blue).

Any color is identified by a unique $\Delta E$ value which is mathematically expressed by the equation:

$$\Delta E = [(L)^2 + (a)^2 + (b)^2]^{1/2}$$

$\Delta E$ represents graphically the distance between the reference color and the no color point (i.e. centre of sphere L=50, a=0, b=0) of the 3d model.

The ability to see a color through a material (or product) is measured as an index of transparency. If a material is 100% transparent, it is possible to measure the same $\Delta E$ value for the above color alone and through the material. As a reference the color white is used. The closer the color is to the white reference (when both are viewed through the material/product) the less transparent that material (or product) will be considered.

Color Transparency Methodology

Color can measured using the colorimeter MINOLTA mode CR-300 instrument (available from the Minolta Company, Japan) which provides the coordinates L*, a*, b* and from which the $\Delta E$ value can be determined.

The standard colors used in this measurement are the primary colors Cyan, Magenta and Yellow references of PANTONE Color Specifier 747XR and the white calibration reference plate of the calorimeter instrument.

The color grade coordinate values for the material to be tested for each of the color references Cyan, Magenta and Yellow is determined by placing the material above the color specific reference and taking a reading from the colorimeter and calculating $\Delta E$.

For each of the reference colors (rc) the $\Delta E$ value is recalculated by setting the scale such that $\Delta E_{rc}$ result, referred to as $\Delta\Delta E_{rc}$ is zero (i.e. 100% transparent) and that $\Delta E white$ with respect to the reference color is referred to as $\Delta\Delta E_w$ which is 62.2 for example and represents 0% transparency.

This can be represented by the formulae below $$\Delta\Delta E_{rc} = [(L_{rc}-L_{rc})^2 + (a_{rc}-a_{rc})^2 + (b_{rc}-b_{rc})^2]^{1/2} = 0$$

$$\Delta\Delta E_w = [(L_{rc}-L_w)^2 + (a_{rc}-a_w)^2 + (b_{rc}-b_w)^2]^{1/2}$$

The $\Delta\Delta E$ value for the product/transparent region of the product for each reference color ($\Delta\Delta E_p$) is then calculated using the following formula:

$$\Delta\Delta E_p/_{rc} = [(L_{rc}-L_p)^2 + (a_{rc}-a_p)^2 + (b_{rc}-b_p)^2]^{1/2}$$

Transparency of the product for each reference color is determined according to the formula:

$$Transparency = 100 - \frac{\Delta\Delta E_{rc} \times 100}{\Delta\Delta E_p}$$

The total transparency is the average value of the transparency for each reference color i.e.

$$Total\ transparency = 100\frac{Transparency_{cyan} + Transparency_{magenta} + Transparency_{yellow}}{3}$$

EXAMPLE

Pantiliners according to the present invention are described herein after:

Option 1

The pantiliner comprises an apertured polyethylene formed film topsheet (transparent CPM DH® available from BP Chemicals), a spiral layer of adhesive (PM17®, available from Savare), an adhesive hydrogel absorbent core (AGM glue code MP-2257, basis weight 180 gsm, available from Fuller), a nonwoven backsheet without pigment (code W16Fio, basis weight 16 gsm, available from BBA Corovin) and stripes of panty fastening adhesive (HL1461 available from Fuller)

Option 2

The pantiliner comprises an apertured polyethylene formed film topsheet (transparent CPM DHO available from BP Chemicals, Wasserburg-Germany), spiral layer of adhesive (PM17®, available from Savare), a non-woven thermal bonded polypropylene core (polypropylene and super absorbent fibres, code NPS80, basis weight 80 gsm available from BFF, UK), spiral layer of adhesive (PM17®, available from Savare, Milan-Italy), a nonwoven backsheet without pigment (code W16Fio, basis weight 16 gsm, available from BBA Corovin, Peine-Germany) and stripes of panty fastening adhesive (HL1461®, available from Fuller, Luneburg-Germany).

| | Results | | | | | |
|---|---|---|---|---|---|---|
| | L* | a* | b* | $\Delta E$ | $\Delta\Delta E$ | Transparency |
| CYAN reference color | 59.8 | −17.7 | −44.7 | 76.7 | 0.0 | 100% |
| Current Alldays | 91.2 | −0.76 | −2.0 | 91.2 | 62.2 | 10% |
| Transparent PL opt 1 | 72.2 | −4.47 | −17.6 | 74.5 | 32.6 | 48% |
| Transparent PL opt 2 | 68.9 | −5.38 | −24.1 | 73.2 | 25.8 | 59% |
| Reference WHITE color | 97.5 | −0.22 | 1.5 | 97.5 | 62.2 | 0% |

-continued

| Results | | | | | |
|---|---|---|---|---|---|
| | L* | a* | b* | ΔE | ΔΔE$_M$ | Transparency |
| MAGENTA reference color | 50.6 | 68.5 | 3.5 | 85.3 | 0.0 | 100% |
| WHITE reference color | 97.5 | −0.22 | 1.5 | 97.5 | 83.2 | 0% |
| Current Alldays | 91.1 | 2.82 | 0.3 | 91.1 | 77.2 | 7% |
| Transparent PL opt 1 | 69.8 | 23.89 | 2.9 | 73.9 | 48.6 | 42% |
| Transparent PL opt 2 | 66.9 | 31.71 | 3.9 | 74.1 | 40.3 | 52% |
| | L* | a* | b* | ΔE | ΔΔE$_Y$ | Transparency |
| YELLOW reference color | 89.5 | −13.8 | 101.1 | 135.7 | 0.0 | 100% |
| WHITE reference color | 97.5 | −0.22 | 1.5 | 97.5 | 100.8 | 0% |
| Current Alldays | 93.9 | −0.32 | 5.2 | 94.0 | 96.9 | 4% |
| Transparent PL opt 1 | 87.0 | −6.17 | 44.9 | 98.0 | 56.8 | 44% |
| Transparent PL opt 2 | 88.8 | −6.74 | 47.7 | 101.1 | 53.8 | 47% |

What is claimed is:

1. An absorbing article comprising a liquid pervious topsheet, a liquid impervious backsheet, and an absorbent structure intermediate said liquid pervious topsheet and liquid impervious backsheet, wherein said article is a sanitary napkin or a pantiliner for use in the crotch region of an undergarment, said absorbing article comprising a pair of wings intended for folding around the crotch portion of an undergarment, said wings are comprised of integral extensions of said topsheet and said backsheet, wherein each of said wings are provided with at least one region of transparency.

2. An absorbing article according to claim 1, wherein each entire wing is transparent.

3. An absorbing article according to claim 1, wherein said topsheet and said backsheet are transparent.

4. An absorbing article according to claim 3, wherein said topsheet and said backsheet are free of pigments or colorants.

5. An absorbing article according to claim 1, wherein said article further comprises a blood detection composition.

* * * * *